United States Patent [19]

Frisch

[11] Patent Number: 4,686,973

[45] Date of Patent: Aug. 18, 1987

[54] METHOD OF MAKING AN INTRAMEDULLARY BONE PLUG AND BONE PLUG MADE THEREBY

[75] Inventor: Eldon E. Frisch, Midland, Mich.

[73] Assignee: Dow Corning Corporation, Midland, Mich.

[21] Appl. No.: 659,976

[22] Filed: Oct. 12, 1984

[51] Int. Cl.[4] ............................................... A61F 5/04
[52] U.S. Cl. ................................ 128/92 YZ; 128/325; 128/344; 128/92 R; 623/23
[58] Field of Search .......................... 128/325, 344, 92; 128/92, 325, 344

[56] References Cited

U.S. PATENT DOCUMENTS

| 3,834,394 | 9/1974 | Hunter et al. | 128/325 |
|---|---|---|---|
| 3,889,665 | 6/1975 | Ling et al. | 128/92 |
| 4,213,461 | 7/1980 | Pevsner | 128/348 |
| 4,245,359 | 1/1981 | Stuhmer | 3/1.9 |
| 4,293,962 | 10/1981 | Fuson | 3/1.9 |
| 4,302,855 | 12/1981 | Swanson | 3/1.9 |
| 4,311,146 | 1/1982 | Wonder | 128/325 |
| 4,327,734 | 5/1982 | White | 128/325 |
| 4,341,218 | 7/1982 | Ü | 128/325 |
| 4,344,190 | 8/1982 | Lee et al. | 3/1.9 |
| 4,357,716 | 11/1982 | Brown | 3/1.913 |
| 4,364,392 | 12/1982 | Strother et al. | 128/325 |
| 4,447,915 | 5/1984 | Weber | 3/1.9 |
| 4,462,394 | 7/1984 | Jacobs | 128/92 C |
| 4,471,779 | 9/1984 | Antoshkiw | 128/325 |

FOREIGN PATENT DOCUMENTS 2637119  3/1977  Fed. Rep. of Germany .
57-26128  6/1982  Japan .

Primary Examiner—Gene Mancene
Assistant Examiner—Wenceslao J. Contreras
Attorney, Agent, or Firm—Richard E. Rakoczy

[57] ABSTRACT

This invention relates to a method of making an inflatable bone plug for plugging the open end of an intramedullary bone canal which is capable of restricting the flow of bone cement, particularly, during the insertion of bone cement, particularly during the pressurized injection of such a cement, during an operative procedure involving the fixation of the stem of an artificial joint prosthesis such as a femoral hip joint prosthesis to the end of a bone such as a femur. The bone plug is designed to be pressurized with a biocompatible fluid and to thereafter deflate in a controlled manner after the cement hardens. Preferably, the bone plug is made by forming a hollow expandable container of a silicone elastomer permeable to carbon dioxide gas which has a valve stem attached to one end of the container and an opening at the opposite end of the container. A shrinkable elastomeric band is placed over the valve stem in which a channel has been made to receive a further cooperating injection means such as a needle. The elastomeric band shrinks over the valve stem to form a resealable valve assembly. The valve assembly is located in the hollow interior of the bone plug and the opening opposite the valve stem is sealed to complete construction of the bone plug. When such a plug is inflated with a biocompatible fluid such as carbon dioxide, the plug remains pressurized for a sufficient amount of time to allow the cement to harden, but the pressure drops to a minimum within about 24 hours after inflation.

22 Claims, 9 Drawing Figures

METHOD OF MAKING AN INTRAMEDULLARY BONE PLUG AND BONE PLUG MADE THEREBY

BACKGROUND OF THE INVENTION

This invention relates to a method of making an inflatable intramedullary bone canal plug for plugging an open-ended intramedullary canal of a bone which is capable of restricting the flow of bone cement after inflation, particularly during the pressurized injection of bone cement, during a procedure involving the implantation of a joint prosthesis to the end of a bone and to the bone plugs made by that method. The bone plug prepared by this method is further capable of deflating in a relatively short period of time after the cement hardens to avoid possible weakening of the cortical bone surrounding the inflated bone plug.

Degenerative bone diseases and injuries to the joints often make it necessary or desirable to replace the natural joint with an artificial prosthesis. One such replacement involves the fixation of an artificial hip joint prosthesis to the proximal end of the femur. The femur contains a hollow intramedullary bone canal running through its central long axis. It is desirable to affix a hip joint prosthesis to the femur in such a manner that the stem of the prosthesis lies along the central long axis of the femur. In preparing the proximal end of the femur to receive such a prosthesis, an appropriately sized opening to receive the stem of the prosthesis is made in the proximal end of the femur. That opening normally extends into the intramedullary bone canal approximately along the central long axis of the femur and is wide enough to permit bone cement to be compacted about the stem to secure the prosthesis to the femur.

To prevent bone cement from flowing deeper into the intramedullary bone canal than is necessary, an intramedullary bone canal plug ("bone plug") composed of a piece of the removed femur or a plug of partially cured bone cement has been used to restrict the flow of cement. Likewise various bone plugs having sides which press-fit against the cortical bone forming the canal to form a seal have been proposed in U.S. Pat. Nos. 4,245,359 (Stuhmer, issued Jan. 20, 1981); 4,302,855 (Swanson, issued Dec. 1, 1981) and 4,293,962 (Fuson, issued Oct. 13, 1981). Once in place, press-fit plugs are difficult to remove and if they do not fit tightly enough, the plug can be driven further down the intramedullary canal when cement is injected under pressure. See U.S. Pat. Nos. 4,462,394 (Jacobs, issued July 31, 1984); 4,357,716 (Brown, issued Nov. 9, 1982) and 3,889,665 (Ling, et al.) for examples of pressurized injection of bone cement.

In U.S. Pat. No. 4,344,190 (issued Aug. 17, 1982), Lee, et al. teach a biodegradeble press-fit bone plug which serves to block the flow of bone cement, but later degrades to alleviate pressure against the hard cortical bone forming the intramedullary canal caused by press-fitting the plug in the canal. As a result, the risk of a fracture occurring at the bone plug site is said to be reduced. No mention is made as to the length of time required before a sufficient level of resorption of the plug occurs to release the pressure. Furthermore, there is no way to adjust to tightness of fit other than by plug size selection. Once inserted, the plug appears to be difficult to remove and, once inserted, a less than optimally-fitting plug could be driven deeper into the canal by the pressure of the cement being injected.

One bone plug designed to be securely fastened inside of the intramedullary bone canal is taught in U.S. Pat. No. 4,447,915 (Weber, issued May 15, 1984). The Weber Patent teaches a two piece medullary bone canal plug formed by a deformable and expandable outer body having a jacket formed of a number of segments and a conical expansion body which is pulled into the outer body to expand the outer body. Once pulled together, the two bodies are permanently secured together via serrations of the inside of the outer body and the outside of the expansion body. However, it appears that once the two bodies are secured together, the plug cannot be removed if for some reason that should become desirable. Likewise, if the plug is secured so that too much pressure is exerted against the sides of the intramedullary bone canal, the presence of the plug may increase the risk of fracture as noted in the Lee, et al. Patent above.

None of the above bone plugs are inflatable.

SUMMARY OF THE INVENTION

There appears to be a need for a bone plug which possesses the following characteristics: (a) it should be capable of being used for a variety of intramedullary bone canal or operative opening sizes in a bone for reception of a joint prosthesis; (b) it should be capable of being tightly secured to a controllable degree against the walls of the canal or opening to restrict the passage of bone cement, particularly cement injected under pressure, past the plug even when the bone plug is placed beyond the isthmus of a bone such as in the femur, (c) it should be capable of being removed after securement against the wall prior to the placement of bone cement into the intramedullary bone canal or opening and (d) it should be capable of releasing the pressure against the wall of the canal or opening in a relatively short period of time after the hardening of the bone cement to decrease the risk of bone resorption and remodelling or changes which could result in fracture of the bone due to stresses on the walls of the canal or opening surrounding the plug. The object of this invention is to provide a bone plug possessing such characteristics and a simple, efficient method for making the same.

Bone plugs meeting the above requirements were developed by me as one type of bone plug which can be used in the method described in a U.S. patent application Ser. No. 06/659,975 filed in the name of Darrel W. Haynes entitled "Device And Method For Plugging An Intramedullary Bone Canal" which is filed concurrently herewith, is assigned to the same assignee as the present invention and is hereby incorporated by reference.

Generally, in accordance with the present invention, a hollow inflatable container of an elastomeric material is formed having one side of the container wall which is ultimately intended to face outward upon completion of the bone plug. That side has a configuration which is adapted to be received within an intramedullary canal of a bone. The opposing side of the container wall is ultimately intended to form a hollow interior region within the plug into which a biocompatible fluid is injected to inflate the bone plug. The container wall side which ultimately resides in the interior region has an elongated member attached thereto which extends into the hollow interior region and also has an opening opposite the elongated member. During or after formation of the container, an opening in the container is formed opposite the elongated member and a channel is formed completely through the center of the elongated member and the interior wall side of the container. A further shrinkable elastomeric band is placed over the elongated member which serves as a valve stem and the band is shrunken to compress the elongated member and the central channel to form a resealable valve assembly. The container wall sides are reversed if the elongated member was on the exterior when the container was formed so that the elongated member and thus the valve assembly are located within the hollow interior region of the plug. The opening is sealed with a cooperating endcapping means such as a patch or button of elastomer. The wall of the container must have a sufficient strength and thickness to contain pressure from the injection of a biocompatible fluid into the hollow interior region and the container must further contain a means for the automatic controlled release of the fluid injected to reduce the pressure within the interior region to a minimum within a preselected amount of time after injection of a pressurizing amount of fluid. Preferably, the controlled release means is a container which is made partially, and most preferably, wholly from a material which is permeable to the fluid to be used to inflate the plug, such as when a gas permeable silicone elastomer container is used with a gas such as carbon dioxide or helium. The endcapping means can alternatively be a plug with an elongated tubular member which fits over the valve assembly to stabilize insertion and inflation of the plug. In another alternative embodiment, the endcapping means can have an elongated tubular member which shrinks over the elongated member to simultaneously form a valve assembly and accomplish sealing of the container to form a bone plug.

Miniature detachable balloon catheters which have been used to accomplish the blockage of blood vessels are known and some of these are described in U.S. Pat. Nos. 3,834,394 (Hunter, et al, issued Sept. 10, 1974); 4,311,146 (Wonder, issued Jan. 19, 1982); 4,327,734 (White, issued May 4, 1982); 4,341,218 (Ü, issued July 27, 1982) and 4,364,392 (Strother, et al., issued Dec. 21, 1982). These devices employ a tiny balloon fixed by means of a valve to the end of a long catheter which is passed as a unit through a blood vessel. The balloon is inflated to accomplish blockage of the blood vessel and the catheter is detached. None of these patents suggest plugging the intramedullary bone canal of a bone with such a device. Furthermore, the balloons described therein are generally not intended to deflate by themselves since it would be undesirable to have the balloon released within a vessel as discussed in the White and the Strother, et al. patents. U.S. Pat. No. 4,213,461 (Pevsner, issued July 22, 1980) describes a miniature balloon catheter which has a pin-hole located opposite the cannula to enable a fluid to be dispersed from the site of the pin-hole for diagnostic purposes. The White patent shows the use of an elastomeric band of plastic or rubber material to assist in retaining the inflation pin in the resealable valve, but does not suggest the method of the present invention. The Ling, et al. Patent and the White, et al. Patent describe pressurized cement delivery systems which are used to accomplish pressurized cement delivery with an expandable rubber plug. However, the plug is not left in the canal to restrict the flow of cement further into the canal after the stem is inserted (a conventional bone plug is used for that purpose), but is designed to seal the open end of the femur from outward escape of cement during pressurization. None of these patents suggest the novel method and bone plug made thereby which forms the subject matter of this invention.

BRIEF DESCRIPTION OF THE DRAWINGS

The above and other objects, features and advantages of the present invention will become apparent to those skilled in the art upon examination of the following description of the present invention.

In the drawings:

FIG. 4 shows the container of FIG. 2 as molded and the relative size of the elongated member 24 to elastomeric band 26 (shown in its shrunken state).

FIG. 5 shows finished resealable valve assembly 20 which is attached to what will become the interior wall side of container 12.

FIG. 6 shows container 12 which has been reversed to place valve assembly 20 in the interior region 21 of the container 12 and showing the manner in which the container 12 may be sealed with endcapping means 17.

DETAILED DESCRIPTION OF THE INVENTION

Figure 1:
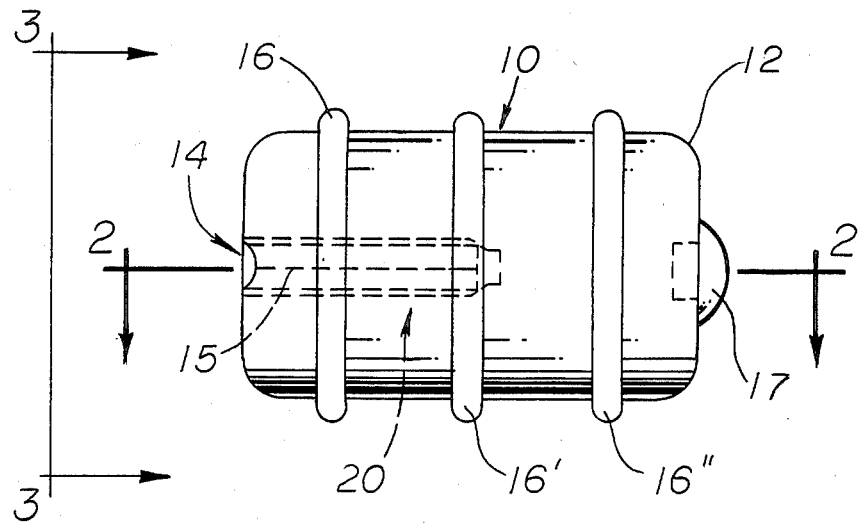
FIG. 1 is a plan view of an inflatable bone plug made by the method of the present invention showing the internal components thereof in relief.

Referring to the drawings, FIG. 1 shows one embodiment of the inflatable bone plug 10 made by the method of the present invention which is shown as a generally cylindrical, almost barrel-like, container 12 having a valve opening 14 at one end, a series of optional raised ribs 16, 16' and 16" on its outer walls to accomplish better sealing against the walls of the intramedullary bone canal and an endcapping means in the form of an end sealing button 17 sealingly fixed to the end by means of an adhesive so that the plug 10 can be inflated with a fluid. Preferably, a simple, flat patch of container material is substituted for button 17. Resealable valve 20 and channel 15 passing completely through resealable valve assembly 20 are shown in relief as dotted lines.

Figure 2:
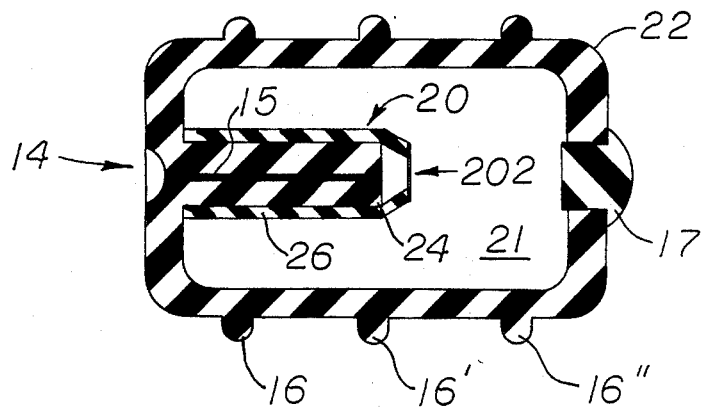
FIG. 2 is a cross-section of the inflatable bone plug of FIG. 1 taken along section lines 2—2.

FIG. 2 more clearly shows the interior region 21 of container 12 in cross-section showing valve opening 14 leading to passage 15 which permits communication between the exterior of container 12 and interior region 21 separated by wall 22 to accomplish pressurization of interior region 21 by injection of a biocompatible fluid. The ends of the container at valve 20 and button 17 are slightly thicker than the remaining container walls to cause expansion along the central long axis of the container. Preferably, the container 12 expands within the intramedullary bone canal along its central long axis such that after pressurization and inflation, the length of the pressurized container 12 running parallel to the central long axis of the bone canal is at least 2 times its diameter. Resealable valve 20 has the advantage of being simple to construct. It is composed of a shrink-fitted elastomeric band 26 surrounding the preferred form of an elongated member shown as cylindrical valve stem 24 with channel 15 running through the middle of stem 24.

Figure 3:
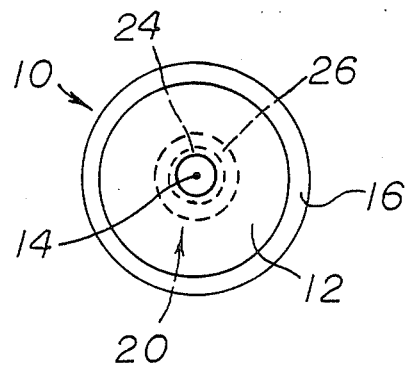
FIG. 3 is an end view of the inflatable bone plug of FIG. 1 as viewed in the direction of arrows 3—3.

FIG. 3 is an end view of plug 10 showing valve opening 14 in container 12 and the relation of internal valve 20 to valve stem 24 and elastic band 26 (shown in relief as dotted lines). Opening 14 is slightly concave with passage 15 at the lowest part of the concavity.

To be useful in the aforementioned Haynes method for plugging the intramedullary bone canal during implantation of a joint prosthesis, the bone plug must be capable of being inflated with a biocompatible fluid, retain its pressure for a sufficient amount of time to function as a seal in the intramedullary bone canal to prevent bone cement from passing by the plug and thereafter release its pressure automatically so as to prevent possible changes in the bone surrounding the bone plug caused by the amount of pressure being exerted by the bone plug against the living bone. Controlled release of the pressure is accomplished by providing the container forming the bone plug with a means for controllably releasing the pressure within the container after inflation that is matched to the permeability characteristics of the fluid being used to inflate the bone plug. The preferred method of making bone plugs of the present invention involves the selection of a container material which is permeable to the biocompatible fluid selected for pressurizing and inflating the container forming the inflatable bone plug. In such a preferred embodiment, at least a portion and preferably the entire container is constructed of a material which is sufficiently permeable to the fluid being injected that the fluid will permeate through the material and cause the pressure of the interior region of container 12 to drop to a minimum within 24 hours after pressurization. The container material 22 or permeable portion thereof must not be so permeable to the fluid that the container cannot retain its pressure for a sufficient period of time to allow a surgeon to complete the insertion of the prosthesis stem and to permit the cement to harden. Medical grade silicone elastomers which are commercially available from Dow Corning Corporation, Midland, Mich. 48640 under the registered trademark "SILASTIC" are one example of biocompatible materials which are useful to form such a container. Examples of other silicone elastomers can be found in the patent literature. Polyurethane or other biocompatible elastomeric materials could also be used to construct the container as long as a suitable means for reducing the pressure is present. Silicone elastomers are preferred and, of those, silicone elastomers having good resistance to tearing are preferred since the exposed bone can abrade the container walls upon insertion.

Examples of fluids which can be used to pressurize the container are carbon dioxide, helium, water or isotonic saline solution with carbon dioxide being most preferred and helium gas being more preferable than a liquid. Fluids that would cause embolisms or other deleterious effects in the body should be avoided. Permeation of nongaseous fluid out of the interior region 21 can be increased through the addition of optional filament (not shown) through endcapping means 17 leading from the interior region 21 to the outside of the plug which can be a stainless steel strand or several strands woven together or one or more strands of a porous or non-porous biocompatible material such as DACRON® polyester. Likewise button 17 or a patch could be of a more permeable material than the remainder of the container 12. These are examples of other means for reducing pressure in the plug. A combination of a container of a substantially polydimethylsiloxane elastomer with carbon dioxide as a pressurizing fluid is presently preferred, based on the inherent high permeability of polydimethylsiloxane elastomer to carbon dioxide as well as its biocompatibility.

Use of a gaseous fluid permits the container to be constructed in a simpler fashion since the entire container can be made of one material. The container wall should be of a sufficient thickness to be able to contain the pressure within interior region 21 without bursting during inflation and should also be sufficiently thick to prevent puncturing or weakening of the walls upon contact with the bone during insertion into the intramedullary bone canal. Silicone elastomers, particularly polydimethylsiloxane elastomers, are therefore quite suitable for use as a container material since their high permeability permits one to select an appropriate wall thickness without substantial loss in permeability. A polydimethylsiloxane elastomer wall thickness of 2 millimeters (mm) (0.08 inches) was found to give good results in testing.

To illustrate the method of carrying out the present invention, a container 12 can be formed as a whole using conventional molding techniques from a medical grade polydimethylsiloxane elastomer having a Die B tear resistance of at least about 200 p.p.i. per ASTM D624; Shore A durometer of about 30-40 per ASTM D2240; tensile strength at break of at least 900 p.s.i., elongation of at least 500% at break, and a 100% modulus of at least 75 p.s.i. per ASTM D412 in such a manner that the valve stem 24 extends away from the rest of container 12 and is located on the wall side of container 12 that will ultimately define the interior region 21 of container 12 shown in FIG. 1.

Figure 4:
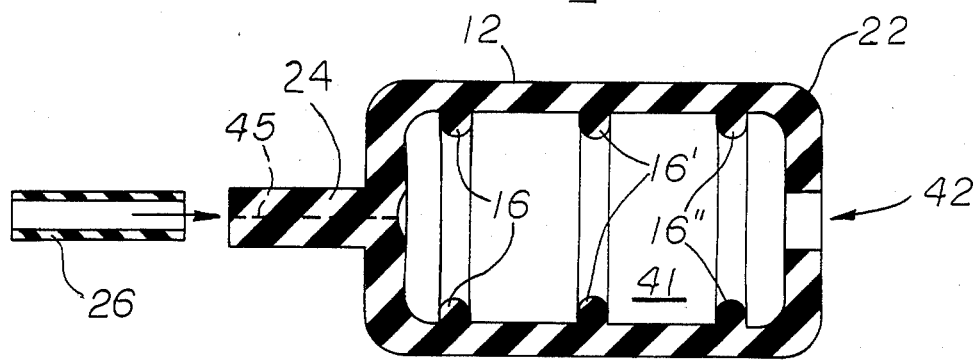
FIGS. 4-6 depict the method by which the bone plug can be constructed.
Figure 6:
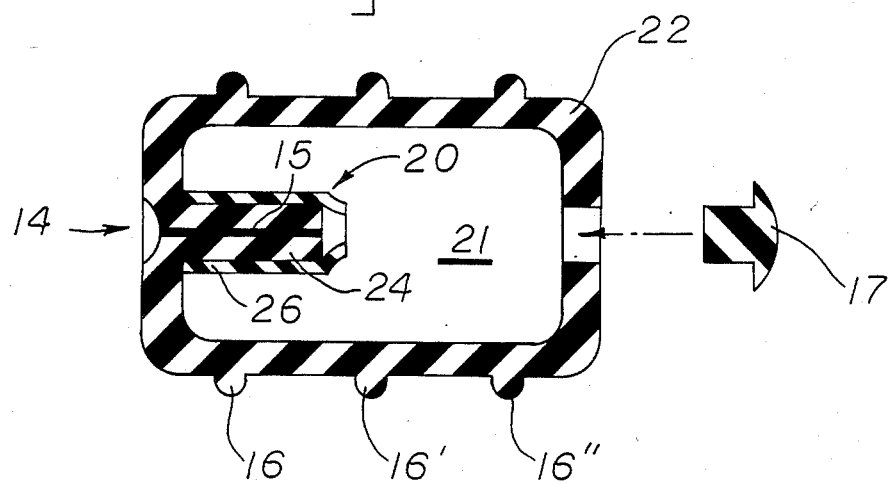

As shown in FIG. 4, what will ultimately become the exterior wall side of plug 10 having raised ribs 16, 16' and 16" defines a hollow interior region 41 in the container as molded. An opening 42 is located at a region opposite valve stem 24 and is at least substantially as wide as the width of the elongated member so as to permit the container walls to be reversed as shown in FIG. 6 such that valve stem 24 is located within hollow region 21 in the completed bone plug 10. Opening 42 can be made during the process of forming the container or can be made in the container 12 after it is molded. Opening 42 is at least as wide as the elongated member 24 to enable one to fit a further shrinkable elastomeric band 26 over valve stem 24 when valve stem 24 is formed on the inside of container 12, but is no larger than the width of container 12 at the position where opening 42 is made to enable one to easily seal opening 42.

Figure 5:
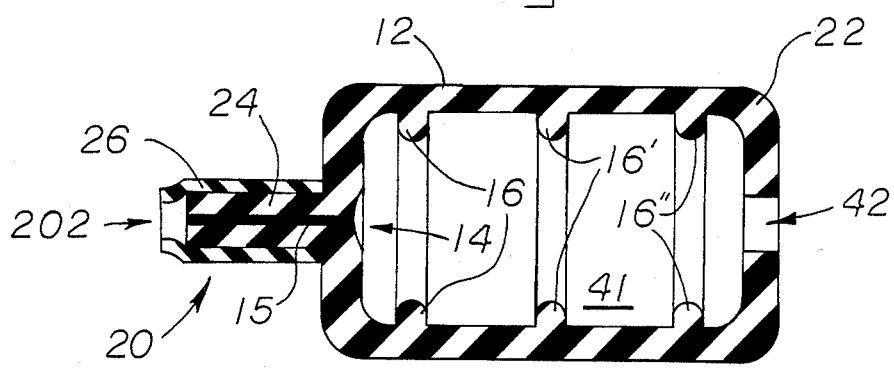
Figure 7:
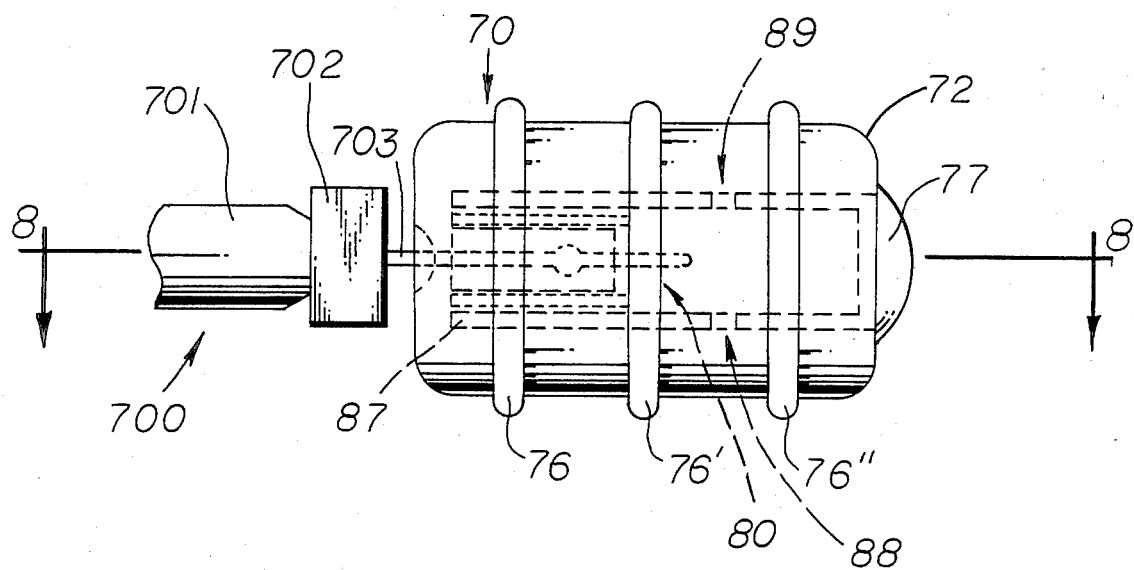
FIG. 7 is a plan view of an alternative embodiment of an inflatable bone plug which contains a central rigidifying rod which is a part of the endcapping means.
Figure 8:
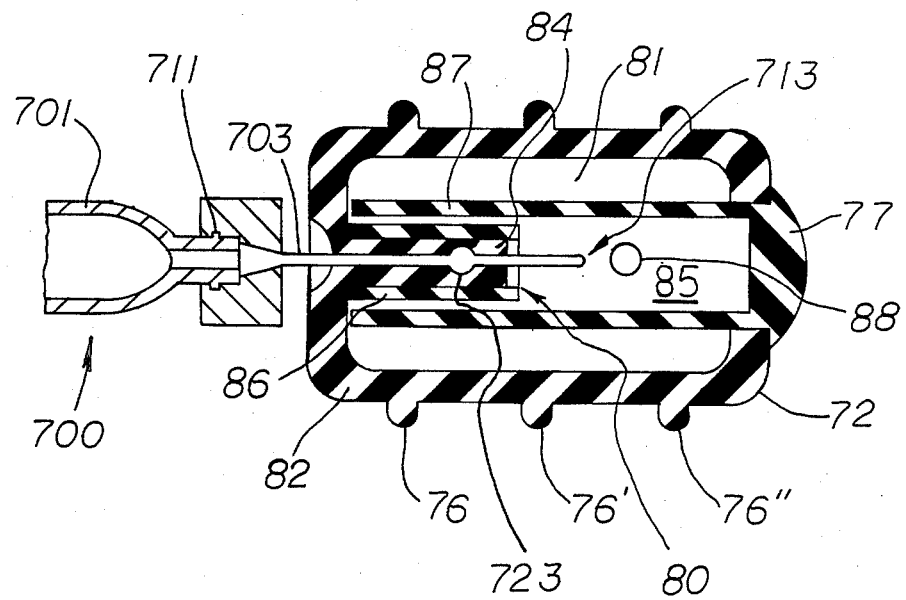
FIG. 8 is a cross-sectional view of the inflatable bone plug of FIG. 7 taken along lines 8—8.

To form resealable valve assembly 20 as shown in completed form in FIG. 5, a channel 15 is made in elongated member 24 through the center 45 of valve stem 24. Channel 15 is prepared by running a needle or other cutting instrument completely through valve stem 24 and exiting through the wall of container 12 at opening 14 and is made so as to be sealingly engageable with a cooperating injection means such as a needle 703 as shown in FIGS. 7 and 8. Channel 15 can be made before or after the elastomeric band 26 is placed over valve stem 24.

A shrinkable elastomeric band 26 of a biocompatible elastomeric material such as one of the same material from which the container is made, preferably of a solvent swollen silicone elastomer, is placed over the valve stem 24. Band 26 has an inner configuration which is larger than the outer configuration of valve stem 24 before shrinking and in its shrunken state is sufficiently smaller than the outside configuration of valve stem 24 that it compresses valve stem 24 and channel 15 running through the middle of valve stem 24 in a sealing fashion, i.e., to a sufficient extent that the channel 15 does not leak fluid after the completed bone plug is inflated. FIG. 4 shows band 26 in its shrunken state and FIG. 5 shows band 26 shrunken around valve stem 24 to form a resealable valve assembly 20 which has an open space 202 through which a needle such as the one shown in FIGS. 7 and 8 makes contact with the interior region 21 of the completed bone plug 10 as shown in FIG. 2. Preferably, a solvent swellable elastomeric band 26 of silicone elastomer, such as one of the same type of elastomer from which the container 12 is made which may additionally contain a radiopaque filler such as barium sulfate to make the implanted plug visible radiographically, which is of slightly smaller inner diameter than the outer diameter of valve stem 24 is swollen in solvent so that it can be fitted over valve stem 24. The solvent is allowed to evaporate or driven off by heating the container so that the band shrinks over stem 24 and forms resealable valve assembly 20.

In the more preferred method shown in FIGS. 4-6, the container 12 is molded such that hollow region 42 is formed by the exterior wall configuration of the completed bone plug to enable the valve stem 24 to be easily molded and thereafter to enable the valve assembly 20 to be easily constructed. In this embodiment, opening 42 is used to reverse the container walls (i.e., the container is turned inside out) so that the container wall side configuration ultimately intended to form the exterior side of bone plug 10 and raised ribs 16, 16' and 16" are on the outside of the container 12 and valve stem 24 and valve assembly 20 are positioned in interior region 21 as shown in FIG. 6.

To complete construction of the bone plug 10, button 17 is adhered to opening 42 by means of a silicone or other adhesive so that interior region 21 can be pressurized. Opening 202 provides an opening where the tip of a needle can extend into region 21 to introduce fluid. In a simpler, more preferred method of sealing the container, a patch of uncured elastomer is placed over the opening 42, the container is placed in a mold and inflated slightly to press the outside of container 12 against the patch and the mold containing the inflated plug is heated to cure the patch and seal the opening 42 in container 12. A polydimethylsiloxane elastomer bone plug which was 20.3 mm (0.8 inches) in length by 11.7 mm (0.46 mm) in diameter having a container side wall thickness of about 2 mm (0.08 inches) was prepared using the above method and tested in human cadavers with good results using carbon dioxide gas as a pressurizing fluid.

Alternatively, the container can be formed with an opening 42 such that the valve stem 24 is located on the interior of container 12 opposite opening 42 such that the container need not be reversed. In this embodiment, the band 26 is pushed through opening 42 which is of a suitable size to enable band 26 to be passed through opening 42 and placed over valve stem 24. In either of these embodiments, shrinking of band 26 may be done before or after the container 12 is sealed.

Another reason that a permeable container is preferred for use in the Haynes method described above is that if a deflation passage or wire braid through button 17 or a deflation passage elsewhere on the container 12 is covered by bone upon insertion (i.e., if the container twists on insertion), release of internal pressure may not occur as rapidly as is desirable. This can be minimized by using the embodiments shown in FIGS. 7-9 which will now be discussed, but it is still preferred that the entire container be permeable to the fluid.

FIGS. 7 and 8 show an alternate embodiment of an inflatable bone plug made by the method of the present invention shown as bone plug 70 which partially shows injection device 700 as tube 701 affixed to connector 702 by means of a conventional twist locking mechanism 711 and with needle 703 inserted through resealable valve 80 so that bulbous portion 723 holds the needle within the valve assembly 80 and hollow tip 713 extends into hollow space 85 which communicates with the hollow interior region 81 of container 72 through apertures 88 and 89 to accomplish pressurization of container 72. Like container 12 of plug 10 shown in FIG. 1, the opening in container 72 is sealed. The manner in which sealing is accomplished renders this embodiment different from those described previously.

Container 72 is constructed in a manner quite similar to that described for container 12 and contains three optional raised ribs 76, 76' and 76". Valve 80 is constructed in the same manner as that described for valve assembly 20 by creating a channel through the center of valve stem 84 and placing an elastomeric band 86 over the valve stem 84 which shrinks over valve stem 84 to form assembly valve 80. In this embodiment, the end-capping means used to seal the opening in the container has a head 77 to which is attached hollow tubular member 87 which extends along the central long axis of container 72 from the end of container 72 opposite valve 80 across to fit over valve assembly 80. This configuration of endcapping means keeps the plug 70 straighter upon insertion so that there is less chance for the plug to turn sideways upon insertion and possibly lose some ability to form an adequate seal against the sides of the intramedullary canal. If desired, the end of portion 87 fitting over valve assembly 80 can also be affixed such as by an adhesive to band 86 of valve assembly 80 to restrict expansion along the central long axis of plug 70 and cause more pressure to be exerted radially from that axis against the sides of the intramedullary bone canal. After insertion over valve assembly 80 by passing member 87 through an opening in wall 82, the inner configuration of tubular member 87 defines a hollow region 85 situated between the end of valve assembly 80 and head 77 into which the tip 713 of needle 703 extends. At least one opening, shown as two openings 88 and 89 in FIGS. 7 and 8, is provided in tubular member 87 between the end of valve assembly 80 farthest from the interior side wall to which it is attached and the interior side of the container wall on which head 77 rests to enable fluid entering region 85 from needle 703 to enter interior region 81 of plug 70 and thereby inflate and pressurize bone plug 70. The hollow tubular member 87 can be made of a biocompatible plastic or an elastomer such as a silicone elastomer.

Figure 9:
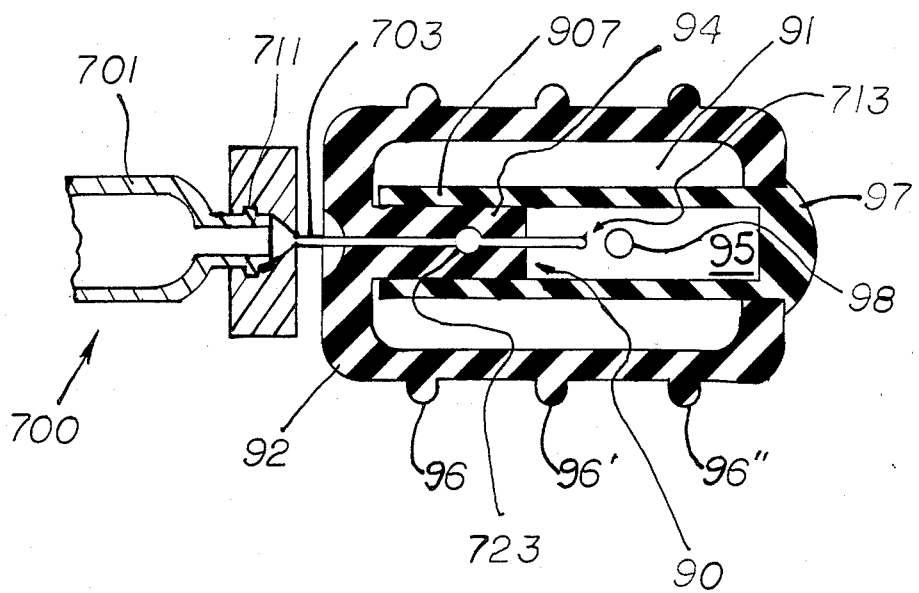
FIG. 9 is a cross-sectional view of a further alternative embodiment of an inflatable bone plug similar to that of FIGS. 7 and 8 wherein the endcapping means also contains the shrinkable elastomeric band used to form the resealable valve assembly 90.

FIG. 9 shows a further alternative embodiment of the method and bone plug made thereby of the present invention which employs an endcapping means of the same configuration as that shown in FIGS. 7 and 8, but the endcapping means also serves as the elastomeric band which is used to compress the valve stem 94 of container 92 to form a resealable valve assembly 90. The container 92 is made in the same manner as described previously for FIGS. 7 and 8. The endcapping means is composed of a head 97 which is positioned on the exterior wall of container 92 and a shrinkable elastomeric tubular member 907 which is attached to head 97. In its unshrunken state, tubular member 907 has an outer configuration which is adopted to pass through the opening in container 92 and has an inner configuration which extends over valve stem 94 during the sealing of the container. After shrinking, the tubular member 907 has an inner configuration which is sufficiently smaller than the outer configuration of the valve stem 94 so as to compress the valve stem 94 and the channel running through the center of the valve stem 94 in a sealing fashion as described previously for elastomeric band 26 to produce a valve assembly 90 after tubular member 907 shrinks around valve stem 94. The same type of materials and means for shrinking elastomeric band 26 can be used for tubular member 907. As described for the endcapping means shown in FIGS. 7 and 8, tubular member 907 forms an interior region 95 into which needle 703 extends and at least one opening 98 is provided to enable fluid injected through needle 703 into region 95 to enter interior region 91 and inflate container 92. Thus, banding, shrinking and sealing in this embodiment are accomplished in a very short period of time and the tubular member 907 serves to rigidify the center of the bone plug and also causes it to exert more pressure radially from the center of the bone plug against the bone surrounding the plug for a more effective seal. Any of the aforementioned endcapping means may contain pigments to indicate the proper end to be inserted within the canal and could also contain radiopaque filler to show the positioning of the bone plug after implantation. The method of using bone plugs produced by the present invention was briefly described above and is more fully described in the aforementioned Haynes Patent Application.

Other modifications and variations of the inflatable bone plug and method of making the same will become apparent to those skilled in the art from an examination of the above specification and drawings. Thus, other variations of the inflatable bone plug and method of making the same may be made which fall within the scope of the appended claims even though such variations were not specifically discussed above.

That which is claimed is:

1. A method of making an inflatable intramedullary bone canal plug for plugging an open-ended intramedullary canal of a bone which comprises the steps of:
   (I) forming a hollow expandable container of a biocompatible elastomeric material having (a) a first container wall side having a configuration which forms a hollow interior region within said plug for receiving a pressurizing amount of a biocompatible fluid and has an elongated member of elastomeric material affixed to said first wall side at one end of the container and (b) a second container wall side opposite and part of the same container wall as is the first wall side having a configuration which is adapted to be received within said canal, said container having an opening situated opposite said elongated member which extends completely through said first and second container wall sides, said opening being at least substantially as wide as the width of the elongated member and no larger than the width of the container at the region where the opening is located,
   (II) forming a channel extending completely through the center of said member and through said wall sides, said channel being sealingly engageable with a cooperating injection means,
   (III) placing a shrinkable elastomeric band of a biocompatible elastomeric material over said elongated member, said band having an inner configuration which is larger than the outer configuration of said member before shrinking and in its shrunken state is sufficiently smaller than the outside configuration of the elongated member so as to compress the elongated member and the channel running therethrough in a sealing fashion,
   (IV) shrinking the elastomeric band over the elongated member to form a resealable valve assembly for receiving said injection means, and
   (V) sealing said opening with an endcapping means, wherein said container wall has a sufficient strength and thickness to contain pressure from injection of said biocompatible fluid into the hollow interior region of said container and wherein said container further contains a means for the controlled release of injected fluid to reduce the pressure within said interior region of a pressurizing amount of said fluid.

2. The method as claimed in claim 1 wherein the container has a generally cylindrical shape and the means for controllably releasing the pressure within said container comprises a container wherein at least a portion thereof is manufactured from a material through which the fluid injected is capable of permeating in a controlled manner.

3. The method as claimed in claim 2 wherein the container is manufactured from a silicone elastomer and the fluid to be used in pressurizing the container is selected from carbon dioxide gas and helium gas.

4. The method as claimed in claim 1 wherein Step I comprised the steps of (Ia) forming a container having a hollow interior region and (Ib) thereafter forming said opening in the container wall.

5. The method as claimed in claim 1 wherein in Step (I) the container is formed such that said first wall side configuration and the elongated member attached thereto face outward from said hollow interior region and said second wall side configuration forms said hollow interior region and further includes the additional step of reversing the container through said opening such that said first wall side configuration forms the hollow interior region within the container and said elongated member is located within said hollow interior region.

6. The method as claimed in claim 5 wherein the container has a generally cylindrical shape and the means for controllably releasing the pressure within said container comprises a container wherein at least a portion thereof is manufactured from a material through which the fluid injected is capable of permeating in a controlled manner.

7. The method as claimed in claim 6 wherein the container is manufactured from a silicone elastomer and the fluid to be used in pressurizing the container is selected from carbon dioxide gas and helium gas.

8. The method as claimed in claim 1 wherein said elongated member has a generally cylindrical shape, said band is an elastomeric tube of a smaller inner diameter than the outer diameter of the elongated member and said tube is swollen in a solvent to render its inner diameter larger than the outer diameter of the tube, Step (IV) being accomplished by allowing the solvent to escape to enable the tube to shrink to its original diameter.

9. The method as claimed in claim 1 wherein said endcapping means is composed of a head which is positioned on the second wall side of said container and a tubular member which is attached to said head and is adapted to pass through said opening and extend over said valve assembly, there further being at least one opening in said tubular member between (a) the end of the valve assembly farthest from the first container wall side and (b) the first container wall side opposite the second container wall side on which the head is affixed to permit fluid being injected to enter said hollow interior region in the event that the tubular member is tightly positioned over the valve assembly.

10. The method as claimed in claim 1 wherein said opening is sealed with an endcapping means which is adapted to be received within said opening, said endcapping means being composed of a head which is positioned on said second container wall and a shrinkable elastomeric tubular member which is attached to said head and, in its unshrunken state, said tubular member has an outer configuration which is adapted to pass through said opening and an inner configuration which extends over said elongated member during the sealing step, said tubular member having an inner configuration which, in its shrunken state, is sufficiently smaller than the outside configuration of the elongated member so as to compress the elongated and the channel running therethrough in a sealing fashion, said endcapping means also functioning as said elastomeric band, there further being at least one opening in said tubular member between (a) the end of the valve assembly farthest from the first container wall side and (b) the first container wall side opposite the second container wall side on which the head is affixed to permit fluid being injected to enter said hollow interior region.

11. An inflatable intramedullary bone canal plug for plugging an open-ended intramedullary canal of a bone comprising a plug produced by a method which comprises the steps of:
  (I) forming a hollow expandable container of a biocompatible elastomeric material having (a) a first container wall side having a configuration which forms a hollow interior region within said plug for receiving a pressurizing amount of a biocompatible fluid and has an elongated member of elastomeric material affixed to said first wall side at one end of the container and (b) a second container wall side opposite and part of the same container wall as is the first wall side having a configuration which is adapted to be received within said canal, said container having an opening situated opposite said elongated member which extends completely through said first and second container wall sides, said opening being at least substantially as wide as the width of the elongated member and no larger than the width of the container at the region where the opening is located,
  (II) forming a channel extending completely through the center of said member and through said wall sides, said channel being sealingly engageable with a cooperating injection means,
  (III) placing a shrinkable elastomeric band of a biocompatible elastomeric material over said elongated member, said band having an inner configuration which is larger than the outer configuration of said member before shrinking and in its shrunken state is sufficiently smaller than the outside configuration of the elongated member so as to compress the elongated member and the channel running therethrough in a sealing fashion,
  (IV) shrinking the elastomeric band over the elongated member to form a resealable valve assembly for receiving said injection means, and
  (V) sealing said opening with an endcapping means, wherein said container wall has a sufficient strength and thickness to contain pressure from injection of said biocompatible fluid into the hollow interior region of said container and wherein said container further contains a means for the controlled release of injected fluid to reduce the pressure within said interior region of a pressurizing amount of said fluid.

12. The inflatable intramedullary bone canal plug as claimed in claim 11 wherein the container has as generally cylindrical shape and the means for controllably releasing the pressure within said container comprises a container wherein at least a portion thereof is manufactured from a material through which the fluid injected is capable of permeating in a controlled manner.

13. The inflatable intramedullary bone canal plug as claimed in claim 12 wherein the container is manufactured from a silicone elastomer and the fluid to be used in pressurizing the container is selected from carbon dioxide gas and helium gas.

14. The inflatable intramedullary bone canal plug as claimed in claim 11 wherein Step I comprised the steps of (Ia) forming a container having a hollow interior region and (Ib) thereafter forming said opening in the container wall.

15. The inflatable intramedullary bone canal plug as claimed in claim 11 wherein in Step (I) the container is formed such that said first wall side configuration and the elongated member attached thereto face outward from said hollow interior region and said second wall side configuration forms said hollow interior region and further includes the additional step of reversing the container through said opening such that said first wall side configuration forms the hollow interior region within the container and said elongated member is located within said hollow interior region.

16. The inflatable intramedullary bone canal plug as claimed in claim 15 wherein the container has a generally cylindrical shape and the means for controllably releasing the pressure within said container comprises a container wherein at least a portion thereof is manufactured from a material through which the fluid injected is capable of permeating in a controlled manner.

17. The inflatable intramedullary bone canal plug as claimed in claim 16 wherein the container is manufactured from a silicone elastomer and the fluid to be used in pressurizing the container is selected from carbon dioxide gas and helium gas.

18. The inflatable intramedullary bone canal plug as claimed in claim 11 wherein said elongated member has a generally cylindrical shape, said band is an elastomeric tube of a smaller inner diameter than the outer diameter of the elongated member and said tube is swollen in a solvent to render its inner diameter larger than the outer diameter of the tube, Step (IV) being accomplished by allowing the solvent to escape to enable the tube to shrink to its original diameter.

19. The inflatable intramedullary bone canal plug as claimed in claim 11 wherein said endcapping means is composed of a head which is positioned on the second wall side of said container and a tubular member which is attached to said head and is adapted to pass through said opening and extend over said valve assembly, there further being at least one opening in said tubular member between (a) the end of the valve assembly farthest from the first container wall side and (b) the first container wall side opposite the second container wall side on which the head is affixed to permit fluid being injected to enter said hollow interior region in the event that the tubular member is tightly positioned over the valve assembly.

20. The inflatable intramedullary bone canal plug as claimed in claim 11 wherein said opening is sealed with an endcapping means which is adapted to be received within said opening, said endcapping means being composed of a head which is positioned on said second container wall and a shrinkable elastomeric tubular member which is attached to said head and, in its unshrunken state, said tubular member has an outer configuration which is adapted to pass through said opening and an inner configuration which extends over said elongated member during the sealing step, said tubular member having an inner configuration which, in its shrunken state, is sufficiently smaller than the outside configuration of the elongated member so as to compress the elongated and the channel running therethrough in a sealing fashion, said endcapping means also functioning as said elastomeric band, there further being at least one opening in said tubular member between (a) the end of the valve assembly farthest from the first container wall side and (b) the first container wall side opposite the second container wall side on which the head is affixed to permit fluid being injected to enter said hollow interior region.

21. The method as claimed in claim 1 wherein in Step (I), sad elongated member is affixed by being formed as an integral part of said first wall side.

22. The inflatable intramedullary bone canal plug as claimed in claim 11 wherein in step (I), said elongated member is affixed by being formed as an integral part of said first wall side.

* * * * *